(12) United States Patent
Simmons et al.

(10) Patent No.: US 11,802,871 B2
(45) Date of Patent: Oct. 31, 2023

(54) SYSTEM AND METHOD FOR DEPOSITING ANTISERA IN IMMUNOFIXATION ELECTROPHORESIS

(71) Applicant: HELENA LABORATORIES CORPORATION, Beaumont, TX (US)

(72) Inventors: James Matthew Simmons, Port Neches, TX (US); Jeffrey Allen Spencer, Lumberton, TX (US); Charles David Kelley, Lumberton, TX (US); Gaston Andres Del Pino, Beaumont, TX (US)

(73) Assignee: HELENA LABORATORIES CORPORATION, Beaumont, TX (US)

( * ) Notice: Subject to any disclaimer, the term of this patent is extended or adjusted under 35 U.S.C. 154(b) by 546 days.

(21) Appl. No.: 16/627,376

(22) PCT Filed: Jul. 13, 2018

(86) PCT No.: PCT/US2018/042014
§ 371 (c)(1),
(2) Date: Dec. 30, 2019

(87) PCT Pub. No.: WO2019/018222
PCT Pub. Date: Jan. 24, 2019

(65) Prior Publication Data
US 2020/0217818 A1    Jul. 9, 2020

Related U.S. Application Data

(60) Provisional application No. 62/535,335, filed on Jul. 21, 2017.

(51) Int. Cl.
*G01N 33/561* (2006.01)
*G01N 27/447* (2006.01)
*G01N 35/10* (2006.01)

(52) U.S. Cl.
CPC ..... *G01N 33/561* (2013.01); *G01N 27/44726* (2013.01); *G01N 27/44743* (2013.01);
(Continued)

(58) Field of Classification Search
CPC ....... G01N 27/44726; G01N 27/44743; G01N 33/561; G01N 2035/1039; G01N 35/10;
(Continued)

(56) References Cited

U.S. PATENT DOCUMENTS 2,522,832 A * 9/1950 Loeffler ............. B65D 83/0094
604/407
3,827,305 A * 8/1974 Gilson .................. B01L 3/0224
73/864.18
(Continued)

OTHER PUBLICATIONS

Johnson A (Annals of Clinical and laboratory Science, vol. 8, No. 3, 1978 (Year: 1978).*
(Continued)

*Primary Examiner* — Christopher L Chin
(74) *Attorney, Agent, or Firm* — Jerold I. Schneider; Schneider IP Law

(57) ABSTRACT

An immunofixation electrophoresis applicator system and method deposits antisera in spaced apart locations on a substrate where the antisera is deposited as an elongated bead in a first direction and retained against migration in a direction transverse to said first direction at least by surface tension.

12 Claims, 2 Drawing Sheets

(52) U.S. Cl.
CPC ................ *B01L 2400/0415* (2013.01); *B01L 2400/0421* (2013.01); *G01N 2035/1039* (2013.01)

(58) Field of Classification Search
CPC ......... G01N 2474/10; B01L 2400/0415; B01L 2400/0421
USPC ......... 436/516, 541, 538; 356/344; 435/180, 435/7.1; 422/68.1, 509, 501, 521, 549; 204/600; 73/864.02; 604/285
See application file for complete search history.

(56) References Cited

U.S. PATENT DOCUMENTS

| | | | | |
|---|---|---|---|---|
| 5,185,066 | A * | 2/1993 | Golias | G01N 27/44721 204/616 |
| 5,882,930 | A * | 3/1999 | Baier | G01N 35/1074 422/63 |
| 6,165,541 | A * | 12/2000 | Merchant | G01N 27/44717 427/272 |
| 6,680,208 | B1 * | 1/2004 | Campos-Gonzalez | G01N 33/6803 435/7.92 |
| 2006/0263902 | A1 * | 11/2006 | Pugia | G01N 33/52 436/180 |
| 2009/0269799 | A1 * | 10/2009 | Winkelman | G06T 7/0012 435/29 |
| 2013/0319864 | A1 * | 12/2013 | Guadagno | G01N 27/44743 204/461 |

OTHER PUBLICATIONS

Johnson (Clinical Chemistry, vol. 28, No. 8, 1982) (Year: 1982).*
IPR (International Report on Patentability) for Corresponding PCT Application dated Jan. 30, 2020.

* cited by examiner

SYSTEM AND METHOD FOR DEPOSITING ANTISERA IN IMMUNOFIXATION ELECTROPHORESIS

This disclosure relates to the field of electrophoresis. Electrophoresis is the movement of electrically charged molecules that are placed on or in a support medium and thereafter subjected to an electrical field. The charged molecules migrate through or along the support medium and across the electric field whereby separation of molecules of various sizes depends, at least in part, on their respective size.

Electrophoresis is used to provide analytical information about various biological molecules. It is widely used by medical laboratories for the analysis of a variety of samples such as for example, blood proteins, DNA, RNA, immunoglobins, hemoglobin, cholesterol, lipoproteins, isoenzymes and cerebrospinal fluid proteins (CSF). These samples typically include large molecules or components that have an electrical charge. Electrophoresis allows for the movement of the electrically charged molecules or components when subjected to an electrical field. During electrophoresis, the samples to be tested or analyzed or evaluated are placed on or within a support medium which is connected to an electrical source. The support medium such as a gel provides a solid or semi-solid porous layer or lattice through which the electrically charged molecules migrate across the electrical field. A buffer solution is typically used to submerge the samples and support medium and maintain pH level. The support medium is typically a backing layer treated with a gel substance. One example of a gel commonly used in electrophoresis is agarose.

Electrophoresis systems include a positive electrode and a negative electrode, which are placed in an electrical circuit to create an electrophoretic field between the electrodes. The charged molecules will flow under the influence of the electrophoretic field within the porous structure of the gel based on the attraction of the charge on the molecule toward the electrode having an opposite charge.

In a non-limiting example of an electrophoresis system, samples are placed into one or more sample areas such as wells that may be either intermediate or near one of the two electrodes, such as for example either intermediate the electrodes or closer to the negative electrode or cathode. The term "intermediate" is not intended to refer to the geographic center between the two electrodes. When the electrical field is activated, the electrically charged molecules or components will move across the electrical field based on their attraction to the oppositely charged electrode. The distance that each molecule or component travels across the electrical field will depend on factors such as the respective or relative size or mass of the component or molecule. The separated components or molecules thus form a series of bands on the support medium that may extend from one end of the medium to the other. Viewing of the bands may be aided by various drying and/or staining techniques and/or washing or removal of the buffer solution. Each band typically represents an amount of a molecule or component having a certain size and may be more or less distinct from other bands depending on the concentration of such molecule or component. This procedure is sometimes referred to as protein fraction resolution. The bands may be further examined and analyzed and evaluated by various techniques such as densitometry and/or other methods.

Immunofixation electrophoresis or IFE is a well-known two-stage procedure for detecting the presence of certain proteins such as those in human serum, urine or CSF. The procedure involves, as a first step, protein fraction resolution by electrophoresis as generally described above. As a second step, the soluble antigen in the protein is allowed to react with its antibody (antiserum). The resultant antigen-antibody complexes will precipitate, at a rate dependent upon the proportion of the reactants, temperature, salt concentration and pH. The antigen-antibody complexes are then visualized by staining.

The IFE process referred to in generally terms in the preceding paragraph is described in greater detail in U.S. Pat. No. 5,185,066 issued Feb. 9, 1993, and assigned to Helena Laboratories Corporation of Beaumont, Texas, U.S.A. the entirety of which is hereby incorporated by reference including the references and bibliography listed therein. Apparatus and chemicals for performing IFE have been marketed for some time by Helena Laboratories Corporation of Beaumont, Texas, U.S.A., the assignee of the aforementioned patent. Non-limiting examples of such apparatus marketed by Helena Laboratories Corporation of Beaumont, Texas, U.S.A., include the SPIFE TOUCH and the SPIFE 4000. The Operator's Manuals (D6500140C of November 2016 and D6500141B of July 2017, respectively) are publicly available from Helena Laboratories Corporation of Beaumont, Texas, U.S.A., on-line at www.Helena.com and are hereby incorporated by reference in their entireties.

Typically, in the use of IFE to analyze proteins for patient diagnostic, patient monitoring and patient evaluation, a specimen from a single patient is diluted and then placed in multiple sample or application areas on a single electrophoretic gel plate. The purpose of utilizing multiple sample areas is to enable detection, separately, of total serum protein, and various proteins such as the immunoglobin heavy chains IgG, IgM, IgA and light chains Kappa and Lambda, or other proteins whose presence or absence may be of importance in medical diagnosis.

Previously, a template having separate channels or slots was placed on the gel plate preferably after the electrophoresis step. Then, various antisera, typically the antisera for IgG, IgM, IgA, Kappa and Lambda proteins were placed in their respective channels or slots in the template. If the specific protein was present in the electrophoresed sample, the protein (antibody) would react with the antisera to cause an antibody-antisera precipitation reaction within the respective channel.

The template, in contact with the gel, maintained each antiserum in its intended channel or slot and prevented undesirable migration of antiserum from one channel or slot to an adjacent channel or slot. Thus, the use of the template was both common and desirable in the IFE process.

Therefore, it was common to fill the channels or slots in the template with excess antisera, that is, more antisera than the actual amount necessary for the antisera-antibody reaction to occur. This increased the costs. In addition, the template, if disposable, increased the cost of each IFE test. The template, if reusable, increased the cost and effort of cleaning between successive tests since cleaning a reusable template was necessary in addition to cleaning the apparatus or system or equipment.

Thus, a system, method and apparatus were needed to provide the benefits of the template but without the need for the template.

According to one aspect, the present system, method and apparatus for applying antisera onto the electrophoresed gel in the IFE procedure avoids the need for the conventional template. The system, method and apparatus may also be used in other electrophoresis environments to apply the desired reagents in the desired places on the gel.

Embodiments of the invention will now be described by way of example only, with reference to the accompanying drawings of which:

Figure 1:
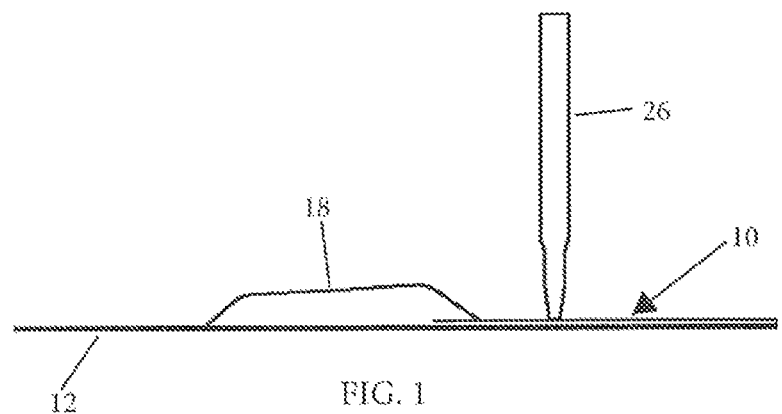
FIG. 1 is an illustration of a pipette or probe in close proximity to an electrophoresis plate or substrate before a bead of reagent is formed.
Figure 2:
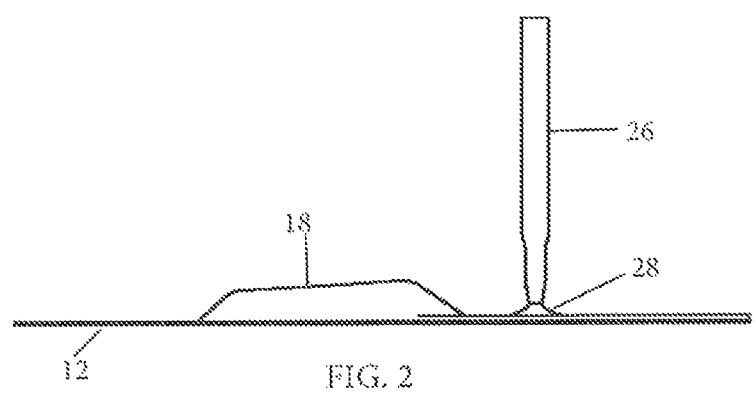
FIG. 2 is an illustration of the use of the pipette or probe to apply a bead of reagent.
Figure 3:
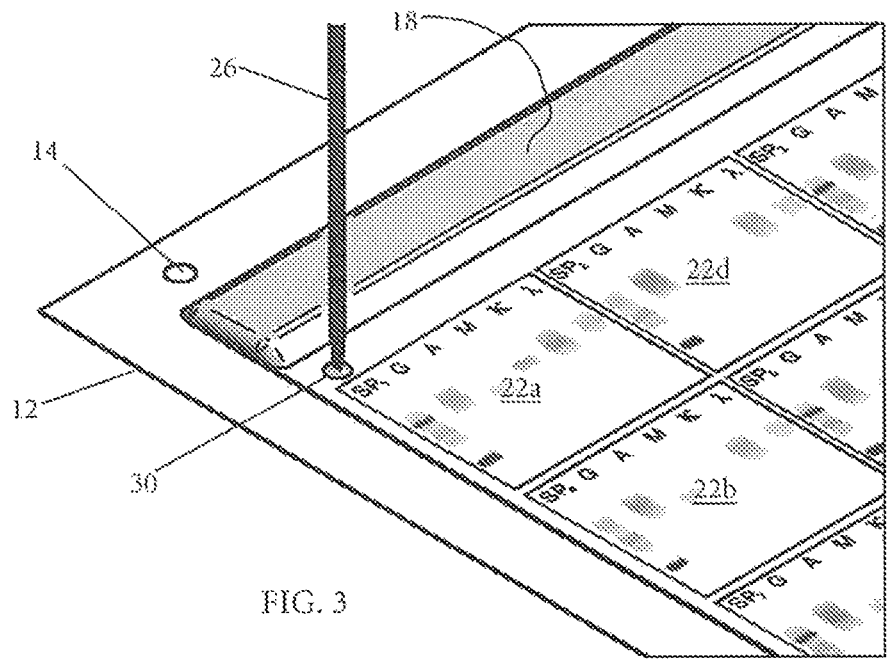
FIG. 3 is a diagrammatic illustration of a portion of an electrophoresis plate showing the beginning of the placement of a reagent on the plate.

With reference to the drawings, an electrophoresis plate 10 is illustrated in diagrammatic form in FIGS. 1, 2 and 3, and includes a backing or substrate which may be a plastic film or sheet 12 such as Mylar® (a trademark of Dupont for polyethylene terephthalate). The sheet includes a series of apertures 14 for alignment with pins in an electrophorese apparatus such as the SPIFE TOUCH manufactured and sold by Helena Laboratories Corporation of Beaumont, Texas, U.S.A. As a non-limiting example, the plate 10 may include an electrophoretic gel 16 such as an agarose gel with enlarged end caps 18, 20 at opposite ends of the gel. The enlarged end caps are also formed of agarose material and are provided to maintain sufficient fluidity during the electrophoresis step.

Solely for the purposes of explanation and in a non-limiting sense, the drawings illustrate how the system may be used to test nine patient samples concurrently. In addition, solely for the purposes of explanation and in a non-limiting sense, the "results" of the immunofixation reactions are illustrated as though the tests have been completed. Thus, test areas 22 for nine patients, designated as 22a, 22b, 22i are illustrated in a three-by-three array in FIG. 4. Test areas 22a, 22b and 22c are arranged in a first column (viewed in the direction from gel end cap 18 to gel end cap 20), a second column to the right of the first column having test areas 22d, 22e and 22f, and a third column to the right of the second column. Again, the number and location and designation of test areas are solely for non-limiting illustrative and explanatory purposes.

In addition, for each patient test area, there are six channels or lanes identified as $SP_x$, G, A, M, K, and λ, referring respectively to the channels for measuring total Serum Protein, IgG, IgM, IgA, Kappa and Lambda. The subscript "x" following SP (as seen in FIG. 3) would, in this non-limiting illustration, range from one to nine since there are test areas for nine patients. The use of the subscript is to assist in identifying and differentiating among the various patients.

Means are provided to deposit patient samples onto the electrophoresis plate preferably intermediate the ends of the six channels for each patient. As may be appreciated, therefore, six samples or aliquots for each patient will be deposited onto the electrophoresis plate and if the samples of nine patients are to be evaluate concurrently, then 54 aliquots will be deposited.

As a non-limiting example, patient samples may be collected, initially in test tubes. The samples are then withdrawn from the test tubes, such as in a laboratory, and deposited into containers or sample cups associated with the electrophoresis system. The samples are subsequently transferred from the sample cups onto the electrophoresis plate using an applicator of the type illustrated in U.S. Pat. No. 6,544,395 granted Apr. 8, 2003 and assigned to Helena Laboratories Corporation of Beaumont, Texas, U.S.A., the entirety of which is hereby incorporated by reference.

Alternatively, a pipette or probe may be used to withdraw patient samples from containers and deposit the patient samples onto the electrophoresis plate. As yet another alternative, a pipette or probe may be used to withdraw patent samples from a test tube and apply the samples directly onto the electrophoresis plate. Other variations in the use of the pipette or probe will be apparent to the skilled worker.

Referring to the FIGS., a pipette or probe 26 is illustrated diagrammatically. The pipette or probe is conventionally used to withdraw patient samples such as from a test tube. If an IFE test is to be performed, the probe would apply six samples from the first patient in the appropriate six channels or lanes on a first test area 22a. The probe would be cleaned and then withdraw samples from a different test tube and apply six samples on test area 22b for a second patient. This process is repeated based on the number of test areas 22 on the electrophoresis plate. Alternatively, a plurality of pipettes or probes may be used concurrently, such as one pipette or probe for each patient.

After the electrophoresis step is completed, the pipette or probe is then used to apply the antisera or reagents onto the plate. The reagent is formed as a bead 28 and is applied preferably along the length of the plate 10 starting at one end 30 of the electrophoresis plate, adjacent one gel end cap 18, and ending at the opposite end 32 of the electrophoresis plate, adjacent the other gel end cap 20.

As a non-limiting illustration based on the preceding paragraph a bead 28 is applied by movement of the probe 26 in the direction of arrow 34, from one end 30 to the other end 32, and the bead 28 appears as a narrow, elongated strip.

Figure 4:
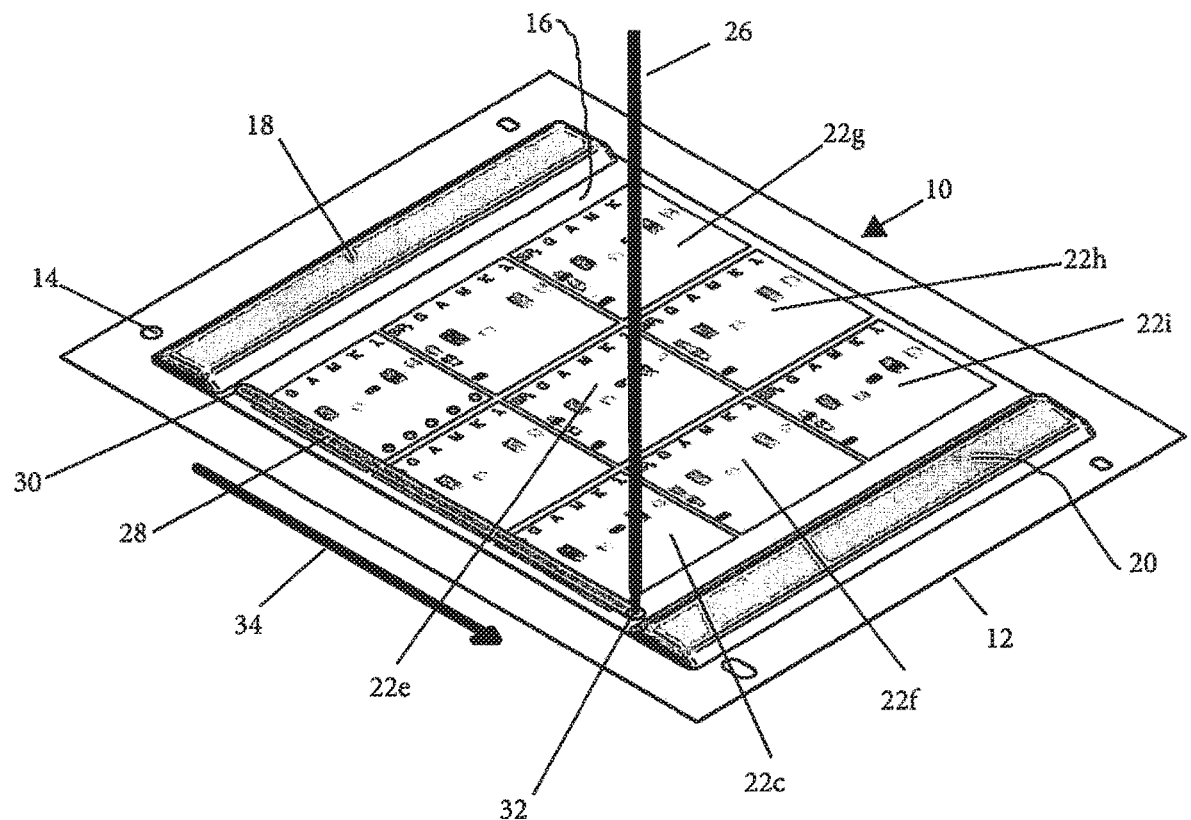
FIG. 4 is a diagrammatic illustration of an electrophoresis plate showing the placement of a reagent on the plate.
Figure 5:
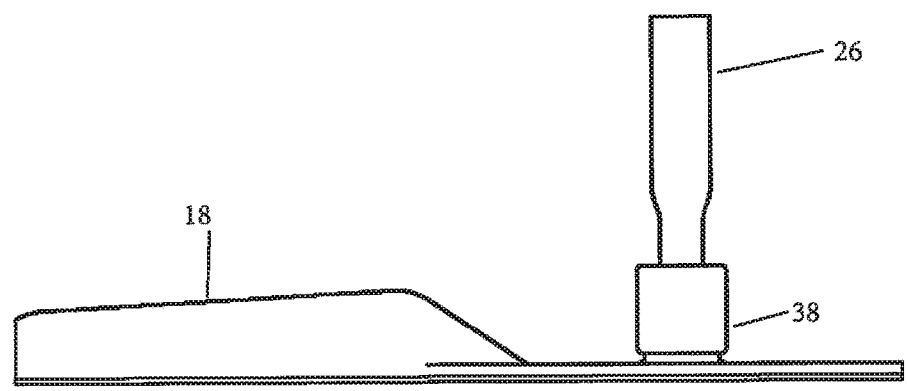
FIG. 5 is a diagrammatic illustration of a modification of the pipette or probe.

In FIG. 4, the bead 28 is illustrated as applied over the SP channel for three test areas 22a, 22b and 22c. Then the probe is removed from contact with the plate 10, such as by raising the probe vertically. The probe is then moved in a direction perpendicular to the direction of the arrow 34, that is, perpendicular to the direction of application of the bead 28. Then, the probe is moved into contact with the plate such as by lowering the probe vertically and a second bead would be applied over the SP area for the next three test areas 22d, 22e and 22f, such as by movement of the probe between ends 30 and 32 of the plate. The skilled worker understands that for the application of the second bead, it may be advantages to reverse the direction of movement of the probe such as from end 32 to end 30 although the probe may be moved to end 30 and then be lowered into contact with the plate for the application of the second bead.

The procedure just described would then be repeated for the non-limiting example illustrated in FIG. 4 where there are three columns of patient test areas, that is, a 3×3 array of patient test samples. In the embodiment illustrated in FIG. 4, there are nine patient test areas, so the probe or pipette would traverse the plate three times just to apply the bead (reagent) for the SP area.

Then, the probe is washed and cleaned. A reagent for the next channel or lane or region of the test area is applied as a discrete bead. In the illustrated non-limiting example the next channel or area will receive the antisera for IgG and this will be applied on test areas 22a, 22b, and 22c, by movement of the probe between ends 30 and 32 of the plate. This is repeated for the next column of test areas, 22d, 22e and 22f and then for the third column of test areas 22g, 22h and 22i. Again, three beads are applied. Then the probe is washed and cleaned and yet another bead is applied, this bead would be the antisera for IgM, and this also is repeated three times, one for each of columns of test areas.

The procedure as just described is then repeated for the antisera for the IgA and Kappa and Lambda test areas. For the illustrated but non-limiting example of an IFE test, six beads or deposits of reagent are required for each test area 22 one reagent for each channel, with the six reagents being correlated to react with the antibody in the patient sample which is to be detected by an antigen-antibody reaction. There are six channels per patient thus six beads are required for each patient, one bead for each channel. In addition, since the array of patient test areas is illustrated as 3×3, each test area includes six channels. Thus, in the non-limiting illustration in a direction perpendicular to the arrow 34 there are 18 channels—six channels for the first column of patient test areas, six channels for the second column of patient test areas and six channels for the third column of test areas.

Therefore, in the illustrated and described but non-limiting example, 18 beads may be deposited, three beads of the antisera of SP, three beads for the antisera to IgG, three beads for the antisera to IgM, etc. Each bead extends between ends 30 and 32 of the plate.

It is also contemplated that multiple probes may be used simultaneously. As a non-limiting example, if three probes are to be used, then all three probes may simultaneously deposit the antisera or reagent for the SP channel, one for test areas 22a, 22b and 22c, a second for test areas 22d, 22e, and 22f, and the third for test areas 22g, 22h and 22i. As another non-limiting example, if six probes are to be used, then the probes may have the reagents for different channels, i.e., one probe having the reagent for the SP channel, a second probe having the reagent for the IgG channel, a third probe having the reagent for the IgM channel, etc. Then, six probes may simultaneously deposit the reagents on the six channels of plates 22a, 22b and 22c while moving between ends 30 and 32, and this is repeated for the second column of test area 22d, 22e, 22f, and then for the third column of test areas 22g, 22h, 22i.

Other sizes and arrays of patient test areas are within the skill of the ordinary worker. The electrophoresis plate may include more or less channels or lanes than the six listed (SP, IgG, IgM, IgA, Kappa and Lambda) for a patient. The electrophoresis plate may include a single patient test area 22. The electrophoresis plate may include only a single column having one or more than one test area, e.g., 22a, 22b, etc., and is not limited to three test areas. The electrophoresis plate may include only a single row having one or more than one test area, e.g., 22a, 22d, etc., and is not limited to three test areas. The overall electrophoresis plate may include an array of patient test areas and is not limited to a 3×3 array.

In a standard IFE procedure, the reactions are visualized after the antisera have been applied and a stain applied. However, to illustrate the relative location of the application of the beads of antisera on the test areas, FIG. 3 also illustrates typical visible reactions in the various columns on various patient test areas, it being understood that in practice the reactions do not occur until after the antisera have been deposited.

The quantity or volume of reagent or antisera that is to be deposited as a bead is controlled. Preferably, but in a non-limiting sense, the volume is controlled by at least one of three techniques. First, the speed of movement of the probe in the direction of application of the antisera may be adjusted and controlled. In an illustrative embodiment the direction of application is in the direction of the arrow 34 from one end of the gel 30 to the other end of the gel 32. Second, the flow rate of reagent or antisera supplied to the pipette or probe from a pump that is used to supply the reagent may be adjusted and controlled. Third, the cross-sectional area of the opening of the pipette or probe may be controlled such as by using probes having openings of different sizes if desired.

In this last regard, it may be appreciated that a probe may include a sharp point or end to puncture a protective cap covering the patient sample. The probe, after puncturing the cap, extends into the sample and withdraws sample for subsequent deposition on the gel. Typically, a probe that punctures the protective cap and applies the patent sample has too small a cross-sectional area opening to apply the desired quantity of antisera. Therefore, a sleeve 38 may be affixed to the end of the probe prior to the application of the beads of antisera. The sleeve may be force-fit onto the probe and may have an open lower end of larger diameter and thus larger cross-section than the cross-sectional area of the probe that is used to puncture the protective cap and/or to apply the patient sample. Thus, the inner diameter of the sleeve may be greater than the outer diameter of the probe. The sleeve assists to limit or control the diameter of the bead as applied on the gel plate. The use of the sleeve is optional if desired to assist in controlling the quantity of antisera to be deposited.

Regardless of whether a sleeve is utilized, the antisera as deposited may spread transverse to the direction of the movement of the probe/sleeve, that is, the antisera may spread transverse to the direction of arrow 34. In one embodiment, the antisera bead as applied will have a width perpendicular to the direction of arrow 34 of approximately 0.432 cm. The antisera bead as applied will have a height above the gel plate generally less than the width.

The system, method and apparatus as described allows the various antisera to be deposited in spaced apart lanes or channels or areas on the gel plate in sufficiently large quantity to provide a reaction if the appropriate antibody is present in the sample but without the need of an external physical barrier such as a template to maintain separation as between the antisera of adjacent channels. The system, method and apparatus utilize less antisera than previously used with a template while providing the same sensitivity. The viscosity of the antisera and reagents may be the same as previously used with a template and, since less antisera is utilized when compared to prior systems, then at least to some extent surface tension maintains, or aids in maintaining, the antisera bead in the proper location free of undesirable migration to adjacent channels.

A suitable syringe pump is the Cavro Centris Pump as described in the Operating Manual 30038165, Revision B, March 2012, publicly available from Tecan Systems of San Jose, California, U.S.A., the entirety of which is hereby incorporated by reference. The movement of the probe in the X, Y and Z directions per se is traditional as used in various products of Helena Laboratories Corporation of Beaumont, Texas, U.S.A.

Many changes and modifications may be made without departing from the spirit and scope of the present disclosure. The disclosure should be limited only by the following claims.

The invention claimed is:

1. A method for detection of at least one antibody in a patient sample, the patient sample being placed on a substrate in a first patient sample test area, the substrate having at least first and second adjacent patient test areas, the method including depositing at least one antisera to the at least one antibody in at least said first patient sample test area to contact the first patient sample test area and to react with the at least one antibody if said antibody is present in the first patient sample test area, the improvement comprising:

said first patient sample test area being free of non-liquid physical boundaries that, if present, would restrict movement of the patient sample, and depositing the at least one antisera in a first direction as an elongated bead along the first patient sample test area of the substrate, the antisera bead being retained on the substrate by surface tension to avoid migration of the antisera in a direction transverse to said first direction.

2. The method according to claim 1, wherein the antisera bead is retained on the substrate by surface tension to avoid migration of the antisera into said second adjacent patient test area.

3. The method according to claim 2, wherein the antisera deposited as an elongated bead on second patient sample test area is different than the antisera deposited as an elongated bead on the first patient sample test area.

4. The method according to claim 1, wherein the second patient sample test area is free of non-liquid physical boundaries that, if present, would restrict movement of the patient sample, and depositing at least a second antisera as an elongated bead on the second patient sample test area of the substrate, the second antisera bead being retained on the substrate by surface tension to avoid migration of the second antisera toward the first patient sample test area.

5. The method according to claim 4, wherein the second antisera is deposited as an elongated bead on the second patient sample test area in a second direction opposite to said first direction.

6. The method according to claim 1, wherein the at least one antisera is deposited as two elongated beads, a first elongated bead on the first patient sample test area and a second elongated bead on the second patient sample test area.

7. The method according to claim 1, wherein multiple elongated beads are deposited sequentially.

8. The method according to claim 1, wherein the at least one patient sample is deposited on the first patient sample test area prior to depositing the at least one antisera in a first direction as an elongated bead, and electrophoresing the at least one patient sample prior to depositing the at least one antisera in a first direction as an elongated bead.

9. The method according to claim 1, wherein the elongated bead has a width greater than the width of the first patient test sample measured in a direction perpendicular to said first direction.

10. The method according to claim 1, wherein the antisera has a speed at which it is deposited, a rate of flow at which it is deposited, and a cross-sectional area at which it is deposited, the method further including controlling at least one of (a) the speed of movement of depositing the antisera in said first direction, (b) the rate of flow of the antisera, and (c) the cross-sectional area of antisera, to control a volume of antisera being deposited as an elongated bead.

11. The method according to claim 10, wherein the volume is controlled such that the width of the elongated bead measured in a direction perpendicular to the first elongated direction is approximately 0.432 cm.

12. The method according to claim 1, wherein the elongated bead is deposited such that the width of the elongated bead measured in a direction perpendicular to the first elongated direction greater than the height of the antisera measured from the substrate.

* * * * *